(12) United States Patent
Banian et al.

(10) Patent No.: US 9,341,060 B2
(45) Date of Patent: *May 17, 2016

(54) METHOD AND SYSTEM FOR PERMEABILITY CALCULATION USING PRODUCTION LOGS FOR HORIZONTAL WELLS

(71) Applicant: KUWAIT OIL COMPANY, Ahmadi (KW)

(72) Inventors: Hassan A A Banian, Ahmadi (KW); Khalaf Gh O H D Alenezi, Ahmadi (KW); Om Prakash Das, Ahmadi (KW)

(73) Assignee: KUWAIT OIL COMPANY, Ahmadi (KW)

( * ) Notice: Subject to any disclaimer, the term of this patent is extended or adjusted under 35 U.S.C. 154(b) by 689 days.

This patent is subject to a terminal disclaimer.

(21) Appl. No.: 13/676,543

(22) Filed: Nov. 14, 2012

(65) Prior Publication Data

US 2014/0136116 A1 May 15, 2014

(51) Int. Cl.
*G01N 15/08* (2006.01)
*E21B 49/08* (2006.01)
*E21B 43/30* (2006.01)

(52) U.S. Cl.
CPC ............ *E21B 49/087* (2013.01); *E21B 43/305* (2013.01); *G01N 15/082* (2013.01)

(58) Field of Classification Search
CPC ............ G01N 15/0826; G01N 15/082; E21B 49/088; E21B 49/00; G01V 11/00; G06F 2217/16
See application file for complete search history.

(56) References Cited

U.S. PATENT DOCUMENTS 6,214,175 B1 * 4/2001 Heinemann et al. ...... 204/157.15
7,806,202 B2 * 10/2010 Stewart .......................... 175/48

* cited by examiner

*Primary Examiner* — Elias Desta
(74) *Attorney, Agent, or Firm* — Richard C. Litman (57) ABSTRACT

A method for permeability calculation includes determining fluid properties associated with a horizontal well, relative permeability to oil and relative permeability to water, for the horizontal well, and an approximate upper boundary and an approximate lower boundary of the horizontal well. In accordance with a particular embodiment, the horizontal well may be divided into a plurality of well segments. Actual production logging data associated with the horizontal well may be received at an interface. For each respective well segment, a horizontal permeability is calculated using the fluid properties, relative permeability to oil, relative permeability to water and actual production logging data.

11 Claims, 10 Drawing Sheets

METHOD AND SYSTEM FOR PERMEABILITY CALCULATION USING PRODUCTION LOGS FOR HORIZONTAL WELLS

TECHNICAL FIELD

The present disclosure relates generally to the field of reservoir characterization, well design, and analysis, and more particularly, to a method and system for permeability calculation using production logs for horizontal wells, including its application in advanced dynamic reservoir characterization, and advanced well completion design using a multi-segment, multiphase horizontal well model.

BACKGROUND OF THE INVENTION

Adequate effective reservoir characterization is important for effective development of oil and gas reservoirs. Further, the knowledge of formation properties such as permeability, porosity, water saturation etc. may be important for effective well completion design. This may be particularly true for Inflow Control Device (ICD) completion design, intelligent completion design, and horizontal and multilateral well designs. Also, effective reservoir management in an attempt to optimize the production and oil recovery often depends upon good dynamic reservoir characterization. Among all formation properties, permeability (or fluid conductivity) is often the most difficult to determine or predict, and has been a long-standing challenge specifically in the heterogeneous reservoirs having faults, fractures, Vugs or high conductive flow channels. The general perception is the rock with greater porosity usually correlates with greater permeability, which does not hold true in many cases. For example, a formation with small pore throat size may have highly interconnected pores, but these pores and pore channels are too small and the paths available are too restrictive for fluid movement, which substantially reduces the permeability.

Formation permeability can be directly determined using core plugs in the laboratory, by using a formation fluid tester in a wellbore, or determined with well tests by use of pressure-transient analysis. However, the measured permeability directly from these methods provides permeability at discrete points and has limitations in estimating the permeability continuously across the none-cored wells, particularly in the horizontal wellbore. Also, the amount of core available for direct permeability measurement is typically limited (due to the cost and logistics associated with core sampling), and permeability estimates usually are made by correlations, by use of wireline-log responses. Further, the permeability measured from these sources might have some uncertainty in estimating the permeability at actual reservoir conditions.

Many investigators have attempted to grasp the complexity of permeability function into a model with general applicability. Most of the models developed are empirical models based on the correlation between formation permeability, formation porosity and irreducible water saturation. These empirical models typically involve measuring porosity and irreducible water saturation of the core and developing mathematical models relating porosity and irreducible water saturation to permeability. In order to use this approach, it is desirable to obtain effective porosity, which is the portion of the porosity that is not isolated and is connected to the pore network and therefore can contribute to fluid flow, and irreducible water saturation. These parameters are not available directly from well logs. Instead, they are estimated from other well log data. However, porosity derived from well log data is not necessarily effective porosity, and methods for deriving irreducible water saturation often rely on effective porosity. Furthermore, empirical models developed for certain formations often perform poorly when used in other fields or formations.

SUMMARY OF THE DISCLOSURE

Accordingly, it is desirable to have methods for providing more accurate formation permeability profiles, specifically in the case of horizontal wells.

In accordance with a particular embodiment of the present disclosure, a method for permeability calculation includes determining fluid properties associated with a horizontal well, under downhole production logging conditions, relative permeability to oil and relative permeability to water, for the horizontal well, and an approximate upper boundary and an approximate lower boundary of the horizontal well. The horizontal well may be divided into a plurality of well segments. Actual production logging data associated with the horizontal well may be received at an interface. For each respective well segment, a horizontal permeability is calculated using the fluid properties, relative permeability to oil, relative permeability to water, a trajectory of the horizontal well, completion specifications of the horizontal well, and actual production logging data.

Technical advantages of the present disclosure includes a method that allows for accurate formation permeability estimation for horizontal wells, based on multiphase production logs. In particular, the method estimates permeability profiles, for example on a foot by foot basis, or even, at wireline log scale, from actual multiphase production log data for horizontal wells. This is done using a well deliverability model for multiphase flow by considering the multi-segment horizontal well model based on the generic Darcy's law for multiphase flow.

Further technical advantages include multiphase permeability and proper reservoir characterization that allows for improving inflow control device (ICD) design, design of intelligent well completions, and multilateral well completions, and its long term performance. Improved well completion design may be important for increasing well productivity and improving overall oil recovery.

Other technical advantages are readily apparent to one skilled in the art from the following figures, descriptions, and claims.

BRIEF DESCRIPTION OF THE DRAWINGS

A more complete and thorough understanding of the present embodiments and advantages thereof may be acquired by referring to the following description, taken in conjunction with the accompanying drawings, in which like reference numbers indicate like features, and wherein.

DETAILED DESCRIPTION OF THE DISCLOSURE

The following embodiments are described and/or illustrated to aid in an understanding of the subject matter of this disclosure, but are not intended, and may not be construed, to limit in any way the claims which follow thereafter. Therefore, while specific terminology is employed for the sake of clarity in describing some embodiments, the present disclosure is not intended to be limited to the specific terminology so selected, and it is to be understood that each specific element includes all equivalents which operate in a similar manner.

Figure 1A:
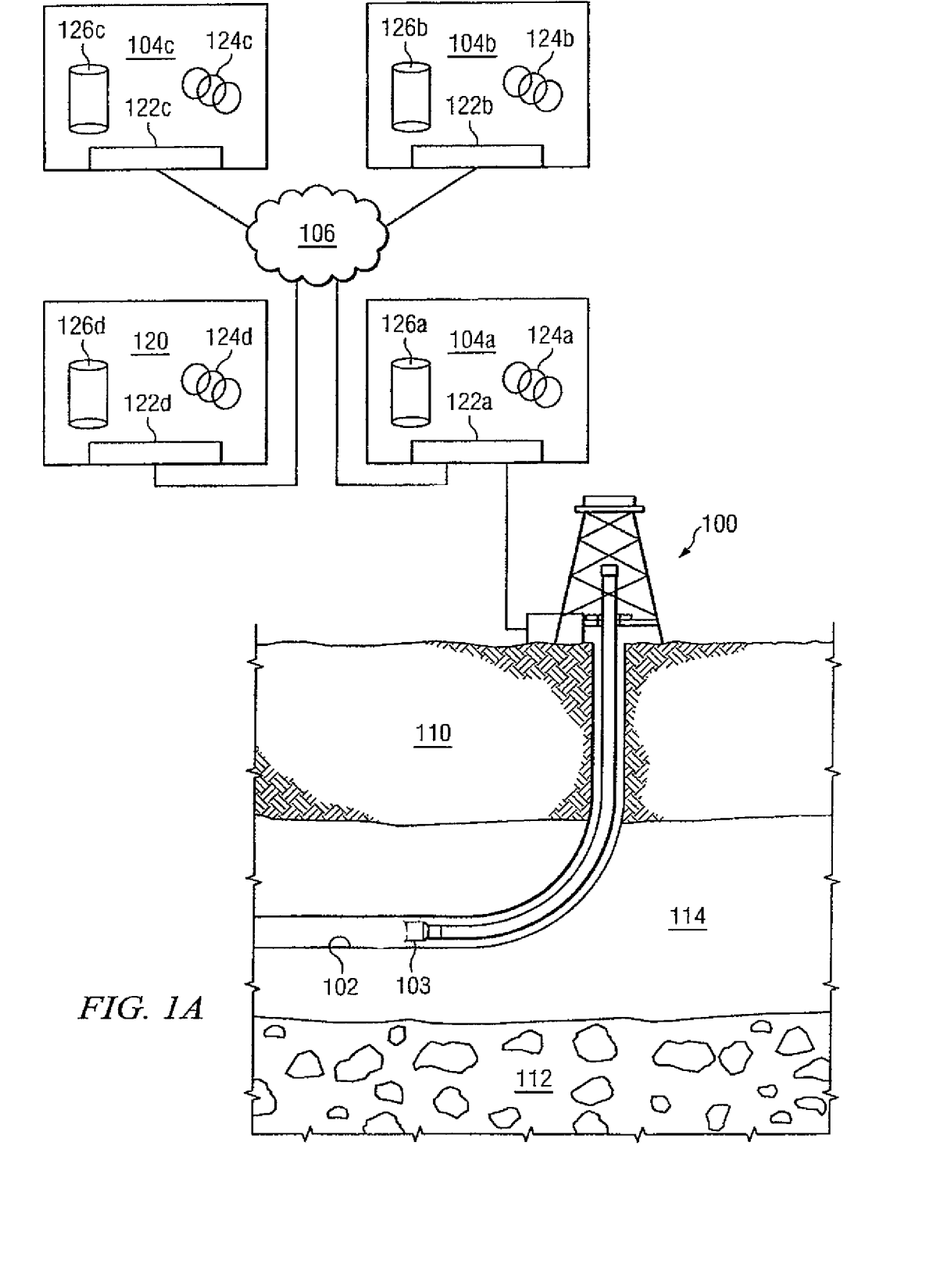
FIG. 1A illustrates a well having a horizontal well section and being in communication with network components, including a system that incorporates aspects of the present disclosure.

FIG. 1A illustrates a well 100 that includes a horizontal segment 102. For the purposes of this disclosure, a "horizontal" well refers to a well or portion of a well that extends generally horizontally with respect to the ground surface or other point of reference. As such, the orientation of the well or well portion is typically at least approximately perpendicular to the force of gravity exerted upon fluids in the formation. However, undulation and/or other imperfections in the horizontal segment (see e.g., FIG. 3) cause deviations in the trajectory and/or geometry of the well. The methodology described herein accounts for such undulations and imperfections to minimize error and uncertainty in permeability calculations of the horizontal well.

Well 100 may include production logging tools and equipment that may be coupled with a computer system 104a. Computer system 104a may be used to receive, collect, analyze, store and/or communicate information regarding well 100 during operation or otherwise.

Computer system 104a may be communicatively coupled with network 106 to allow for network communication to or from computer system 104a. Additional computer systems 104(b) and 104(c) may also be in communication with other components of network 106 to allow communication therebetween. For example, in various embodiments, computer systems 104b or 104c may be associated with a laboratory at which samples are collected and or analyzed. Similarly, computer systems 104b or 104c may be resident at an enterprise that is responsible for the operation of well 100. Finally, computer systems 104b or 104c may be used to compile historical information regarding well 100, areas adjacent to well 100 (e.g., 110, 112 and/or 114), and/or other formations, to allow such data to be used in the equations and analyses referred to below.

In accordance with the teachings of the present disclosure, computer system 120 may be used to accomplish the features, data acquisition, computation, and analysis associated with the methodology of the present disclosure. Each of the computer systems 104a-c and 120 include computer hardware and software components, including an interface 122a-d (hardware interface and/or software interface), processor(s) 124a-d, and memory 126a-d (e.g., memory storage device) to facilitate the features and functions described herein.

The computer systems and components described herein may include input devices, output devices, mass storage media, processors, memory, interfaces, communication ports, or other appropriate components for communicating among computer systems 104a-c and/or 120. For example, computer systems may include a personal computer, workstation, network computer, kiosk, wireless data port, personal data assistant (PDA), one or more Internet Protocol (IP) telephones, one or more processors within these or other devices, or any other suitable processing device. As a particular example, computer system 120, for example may include a computer that includes an input device, such as a keypad, touch screen, mouse, or other device that can accept information, and an output device that conveys information associated with the operation of other computer or network components, including digital data, visual information, or any other suitable information. Both the input device and output device may include fixed or removable storage media such as a magnetic computer disk, CD-ROM, or other suitable media to both receive input from and provide output to a user of the computer systems.

The computer systems may be local to or remote from other computer systems, network components, or well 100. Although a particular number of computer systems are illustrated, the present disclosure contemplates any suitable number of computer systems, according to particular needs.

Each computer system may include a browser or other suitable interface for accessing information over network 106. For example, the browser may present various web-enabled data feeds and receive commands from the computer system. Browser 18 may include any suitable interface for submitting requests for and displaying media such as web pages. It should be understood that the term "browser" may be used in the singular or in the plural to describe one or more browsers and each of the displays of a particular browser.

Network 106 and/or computer systems 104a-104c and/or 120 facilitate wireless or wireline communication. Network 106 may communicate, for example, IP packets, Frame Relay frames, Asynchronous Transfer Mode (ATM) cells, voice, video, data, and other suitable information between network addresses. Network 106 may include one or more local area networks (LANs), radio access networks (RANs), metropolitan area networks (MANs), wide area networks (WANs), all or a portion of the global computer network known as the Internet, and/or any other communication system or systems at one or more locations.

Each computer system includes one or more electronic computing devices operable to receive, transmit, process, and store data associated with computer systems 104a-c and/or 120. For example, each may include one or more general-purpose personal computers (PCs), Macintoshes, workstations, Unix-based computers, server computers, or any other suitable devices. In short, each computer system may include any suitable combination of software, firmware, hardware, and any other suitable components.

Although FIG. 1A illustrates computer system 104a at a position adjacent the well and at the surface of the well, it will be appreciated by those of ordinary skill in the art that computer system 104a may be located anywhere that allows for communication with network 106. Moreover, computer system 104a may also be located downhole during drilling, completion or production operations. In such embodiments, computer system 104a may be coupled with measurement tools or other devices, or may be a stand alone tool (e.g., downhole tool 103) for allowing the permeability calculations to occur in real time as production logging tools are collecting data.

The present disclosure includes the estimation of the permeability profiles, for example on a foot by foot basis or even at wireline log scale, from actual multiphase production log data for horizontal wells (e.g., well section 102). Furthermore, the present disclosure also includes the development of an explicit well deliverability model for multiphase flow, by considering the multi-segment horizontal well model in order to predict the permeability profile across the horizontal well based on the generic Darcy's law for multiphase flow. A brief description of the reservoir inflow with wellbore coupling model is detailed below.

In order to calculate the reservoir inflow, the reservoir drainage area is divided into several sections as per the actual well trajectory of the well. Further, each drainage area is subdivided into small well segments. The bottom of the reservoir drainage area is at the constant pressure boundary or no flow boundary or impermeable boundary of the reservoir and the top of the reservoir drainage area is the impermeable boundary, no flow boundary, or constant pressure boundary.

Figure 1B:
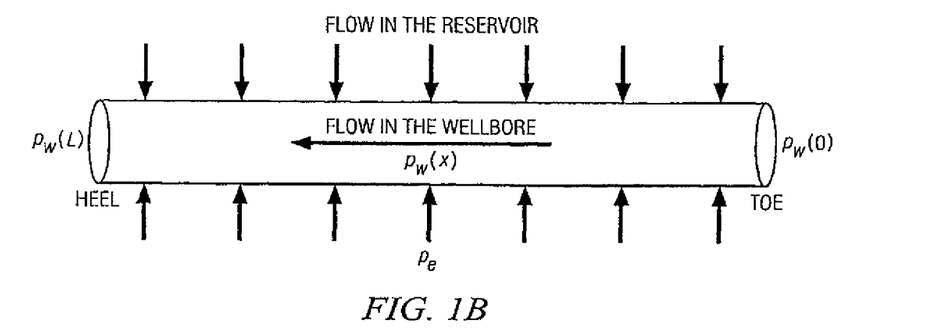
FIG. 1B illustrates a coupling of flow in a reservoir and flow in the wellbore of the horizontal well section of FIG. 1A, in accordance with a particular embodiment of the present disclosure.

The reservoir inflow is coupled with wellbore model for finite conductive horizontal well as shown in FIG. 1. The flow from the reservoir is assumed perpendicular to the wellbore at all locations of the wellbore and no component of the flow is parallel to the wellbore. This is the most likely case for a horizontal well production with either open hole completion or with cased cemented and perforated completions.

Assuming "$P_e$" is the pressure at the outer boundary of the reservoir and $P_w(x)$ is the pressure along the wellbore, i.e. Flowing Bottom Hole Pressure (FBHP).

The well inflow equation can be written as:

$$q_s(x) = J_s(x)[P_e - P_w(x)] \tag{1}$$

Where, $q_s(x)$ is the flow in to the well per unit length of the wellbore and $J_s(x)$ is the productivity index per unit length of the well i.e. specific productivity index. The $J_s(x)$ varies along the wellbore because of variation in formation permeability, near wellbore formation damage distribution and anisotropy of the reservoir rock.

Integrating the equation (1) along the entire horizontal wellbore length the total flow rate from the well is:

$$Q = \int_n^L q_s(x)dx = \int_o^L J_s(x)[Pe - Pw(x)]dx \tag{2}$$

Figure 2A:
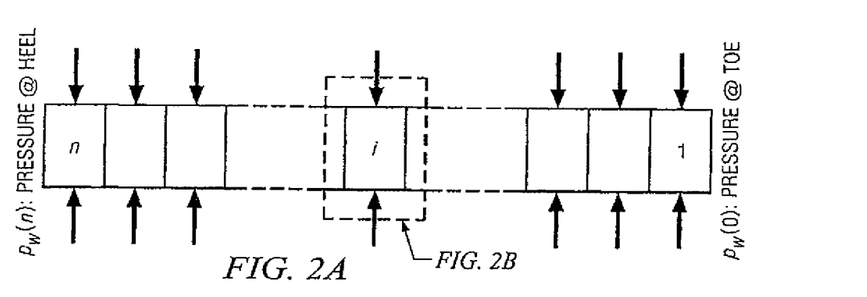
FIG. 2A illustrates a schematic of a segmented horizontal wellbore, in accordance with a particular embodiment of the present disclosure.
Figure 2B:
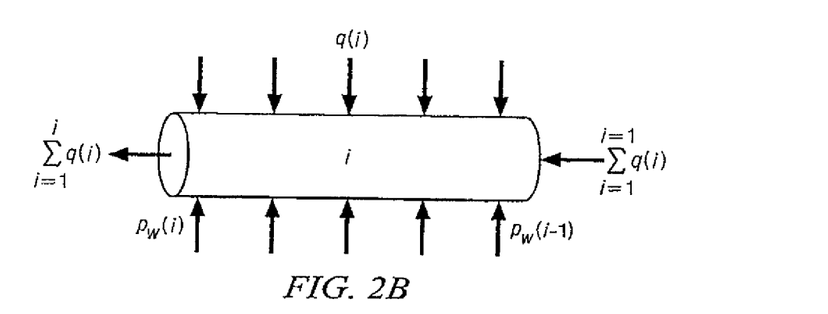
FIG. 2B illustrates a segment of a horizontal wellbore of FIG. 2A, in accordance with a particular embodiment of the present disclosure.

As detailed above, the horizontal wellbore is divided in to several small segments. The schematics of the segmented horizontal wellbore is shown in FIG. 2A. The segments are numbered from "1" at the toe of the lateral to "n" at the heel of the lateral. The total production rate will be the sum of the flow rate from each segment. Each wellbore segment length (e.g., the segment illustrated in FIG. 2B) "Δx" could range from a few inches to a few feet or even at wireline log scale, depending on the analysis requirements.

Therefore:

$$Q = \sum_{i=1}^{i=n} q(i) \tag{3}$$

Where, $$q(i) = J_s(i)\Delta x[P_e - \overline{P_w}(i)] \tag{4}$$

Where, $J_s(i)$ is the specific productivity of segment number i, and $\overline{P_w}(i)$ is the average wellbore pressure at this segment. For steady state flow conditions, the specific productivity index $J_s(i)$ is defined as $$J_s(i) = \frac{7.08 \times 10^{-3} k_k}{\mu B \left[ \ln\left(\frac{h I_{ani}}{r_w(I_{ani}+1)}\right) + \frac{\pi w}{2h I_{ani}} - 0.785 + S(i) + S_r + s_\theta + S \right]} \tag{5}$$

$$I_{ani} = \sqrt{\frac{k_k}{k_v}} \quad \text{and} \quad k_k = \sqrt{k_x k_y} \tag{6}$$

$S(i)$=Near wellbore damage skin factor $S_r$=Partial penetration skin factor $S_\theta$=Slanted skin factor S=other skin factors due to perforation, or due to typical well completions Near Wellbore Damage Skin Factor Applying the elliptical cone shape model for damage distribution along the horizontal well proposed by Frick and Economides (1993), S(i) can be calculated as follows, $$S(i) = \left(\frac{k_k}{k_s} - 1\right) \ln\left[\left\{\left(\frac{2a_{max}}{r_w(I_{ani}+1)} - 1\right)\frac{x(i)}{L} + 1\right\}\right] \tag{7}$$

$$S(i) = \left(\frac{k_k}{k_s} - 1\right) \ln\left[\left\{\left(\frac{2a_{max}}{r_w(I_{ani}+1)} - 1\right)\frac{x(i)}{L} + 1\right\}\right]$$

Here x(i) is the distance between center of segment number i and toe of the lateral.

Slanted Skin Factor

To include the effects of undulations along the horizontal wellbore section, the slanted skin factor is calculated based on the Besson's model. The Schematic of the undulating horizontal wellbore is shown in the FIG. 3.

Besson proposed a slanted well skin correlation from the results of a semi-analytical reservoir simulator. In this model the pay thickness (h) and horizontal well segment length (Δx) are used to represent the slanted angle (θ). The slanted skin factor can be written as, $$s_\theta = \ln\left(\frac{4r_w}{\Delta x I_{ani}\gamma}\right) + \frac{h}{\Delta xy}\ln\left(\frac{2I_{ani}\sqrt{\Delta xh\gamma}}{4r_w(1+1/\gamma)}\right) \quad (8)$$

$$s_\theta = \ln\left(\frac{4r_w}{\Delta x I_{ani}\gamma}\right) + \frac{h}{\Delta xy}\ln\left(\frac{2I_{ani}\sqrt{\Delta xh\gamma}}{4r_w(1+1/\gamma)}\right)$$

Where, $$\gamma = \sqrt{\left(\frac{1}{I_{ani}^2} + \left(\frac{h}{\Delta x}\right)^2\left(1 - \frac{1}{I_{ani}^2}\right)\right)} \quad (9)$$

$$\gamma = \sqrt{\left(\frac{1}{I_{ani}^2} + \left(\frac{h}{\Delta x}\right)^2\left(1 - \frac{1}{I_{ani}^2}\right)\right)}$$

Partial Penetration Skin Factor

Figure 3:
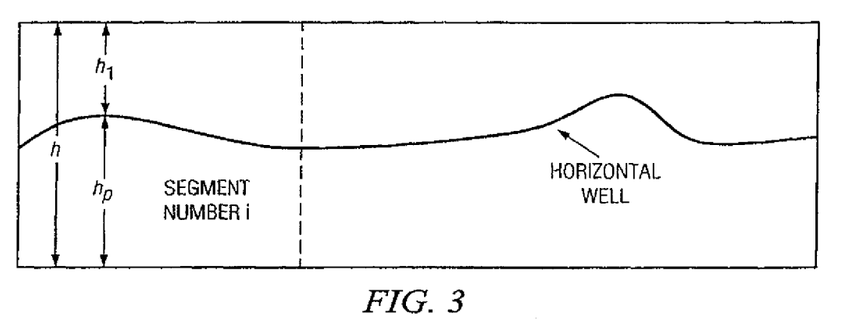
FIG. 3 illustrates a schematic of a horizontal wellbore illustrating undulations in the horizontal well, in accordance with a particular embodiment of the present disclosure.

Since the model assumes that there is a no flow boundary or constant pressure boundary at the top and bottom of the reservoir, so the actual reservoir drainage volume by the horizontal well will be smaller than the total reservoir drainage volume, when the well height ($h_t1$ or $h_tp$) as shown in the FIG. 3, is lower than the reservoir thickness (height) "h". The partial skin factor accounts for these phenomenon.

The partial penetration skin $S_r$, can be calculated using the equation developed by Babu and Odeh (1989).

$$S_r = \left(\frac{1}{h_pD} - 1\right)\ln\left(\frac{\pi}{2r_D}\right) + \frac{1}{h_pD}\ln\left[\frac{h_pD}{2+h_pD}\left(\frac{A-1}{B-1}\right)^{\frac{1}{2}}\right] \quad (10)$$

$$S_r = \left(\frac{1}{h_pD} - 1\right)\ln\left(\frac{\pi}{2r_D}\right) + \frac{1}{h_pD}\ln\left[\frac{h_pD}{2+h_pD}\left(\frac{A-1}{B-1}\right)^{\frac{1}{2}}\right]$$

Where, $h_pD = h_p/h$ and $$r_D = \frac{r_w}{h}\left(\frac{k_v}{k_k}\right)^{\frac{1}{2}}$$

and $A = 1/(h_1D + h_pD/4)$ and $B = 1/(h_1D + 3h_pD/4)$

Relative Permeability Estimation

The relative permeability-vs-water saturation data are usually obtained from displacement experiments with the core flood experiments in the laboratory. The relative permeability curves for oil, water and gas phase for both imbibitions and drainage process is obtained from the core test (e.g., special core analysis, or SCAL) of the various reservoir rocks as well as various flow units of the reservoir. A typical relative permeability curves are presented in FIG. 4.

Figure 4:
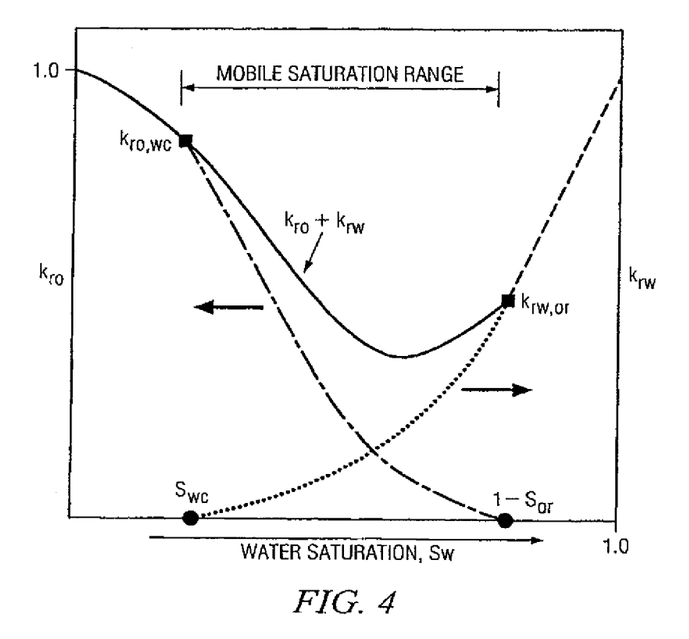
FIG. 4 illustrates relative permeability curves of the horizontal well, in accordance with a particular embodiment of the present disclosure.

However, the water saturation values for each of well segment can be predicted from the sigma logs normally run along with production logging tools. Based on the water saturation values the relative permeability for oil phase and water phase can be obtained, which is required as an input data for the model described in this disclosure.

Two Phase (Oil & Water) Flow Model

The Darcy's law for the oil and water flow for the well segment number (i) can be written as follows:

For the Oil Phase flow rate, the equation (4) for the segment number (i) can be written as $$q_D(i) = J_{so}(i)\Delta x[P_e - \overline{P_{wo}}(i)] \quad (11)$$

For the Water Phase flow rate, the equation (4) for the segment number (i) can be written as;

$$q_w(i) = J_{aw}(i)\Delta x[P_B - \overline{P_{ww}}(i)] \quad (12)$$

Where, the specific productivity index for Oil Phase can be written as;

$$J_{so}(i) = \frac{7.08 \times 10^{-3}k_kK_{ro}}{\mu_o B_o\left[\ln\left(\frac{hI_{ani}}{r_w(I_{ani}+1)}\right) + \frac{\pi w}{2hI_{ani}} - 0.785 + S(i) + S_r + s_\theta + S\right]} \quad (13)$$

$$J_{so}(i) = \frac{7.08 \times 10^{-3}k_kK_{ro}}{\mu_o B_o\left[\ln\left(\frac{hI_{ani}}{r_w(I_{ani}+1)}\right) + \frac{\pi w}{2hI_{ani}} - 0.785 + S(i) + S_r + s_\theta + S\right]}$$

The specific productivity index for Water Phase can be written as;

$$J_{sw}(i) = \frac{7.08 \times 10^{-3}k_kK_{rw}}{\mu_w B_w\left[\ln\left(\frac{hI_{ani}}{r_w(I_{ani}+1)}\right) + \frac{\pi w}{2hI_{ani}} - 0.785 + S(i) + S_r + s_\theta + S\right]} \quad (14)$$

$$J_{sw}(i) = \frac{7.08 \times 10^{-3}k_kK_{rw}}{\mu_w B_w\left[\ln\left(\frac{hI_{ani}}{r_w(I_{ani}+1)}\right) + \frac{\pi w}{2hI_{ani}} - 0.785 + S(i) + S_r + s_\theta + S\right]}$$

By neglecting the Capillary Pressure effects:

Drawdown of oil phase=Drawdown on water phase, $$[P_e - \overline{P_{wo}}] = [P'_e - \overline{P_{ww}}(i)] = \text{Drawdown} = \text{Static BHP from PLT–FBHP from PLT} \quad (15)$$

Where, PLT stands for production log.

Let, $$F(i) = \frac{7.08 \times 10^{-3}}{\left[\ln\left(\frac{hI_{ani}}{r_w(I_{ani}+1)}\right) + \frac{\pi w}{2hI_{ani}} - 0.785 + S(i) + S_r + s_\theta + S\right]} \quad (16)$$

$$F(i) = \frac{7.08 \times 10^{-3}}{\left[\ln\left(\frac{hI_{ani}}{r_w(I_{ani}+1)}\right) + \frac{\pi w}{2hI_{ani}} - 0.785 + S(i) + S_r + s_\theta + S\right]}$$

So, the total flow rate can be written as:

$$q_t(l) = q_o(l) + q_w(l) \quad (17)$$

So, by combining the equations from (11) to (17), we can get the following equation:

$$\left((q_0(i)+q_w(i))/\left(\frac{K_{ro}}{\mu_o B_o}+\frac{K_{rw}}{\mu_w B_w}\right)\right)\left((q_0(i)+q_w(i))/\left(\frac{K_{ro}}{\mu_o B_o}+\frac{K_{rw}}{\mu_w B_w}\right)\right) = \quad (18)$$

$$F(i)*(\text{Static } BHP \text{ from } PLT - FBHP \text{ from } PLT)^{*k_k}$$

From the Production logging data, the oil and water flow rate as well as SBHP and FBHP can be obtained for each segment of the horizontal wellbore as well as for the (i)th segment of horizontal wellbore. The value of F(i) is independent of flow characteristics and calculated based on the actual well and reservoir parameters for each segments of horizontal wellbore. The reservoir fluid properties i.e. viscosity, formation volume factors etc. are obtained from the PVT analysis of the fluids.

Hence by using the equation (18), the horizontal permeability for each horizontal well-segment is calculated. Further the vertical permeability can be predicted from equation (6) by knowing the formation anisotropy factor $[(^\infty 1)]_\perp ani$".

Figure 5:
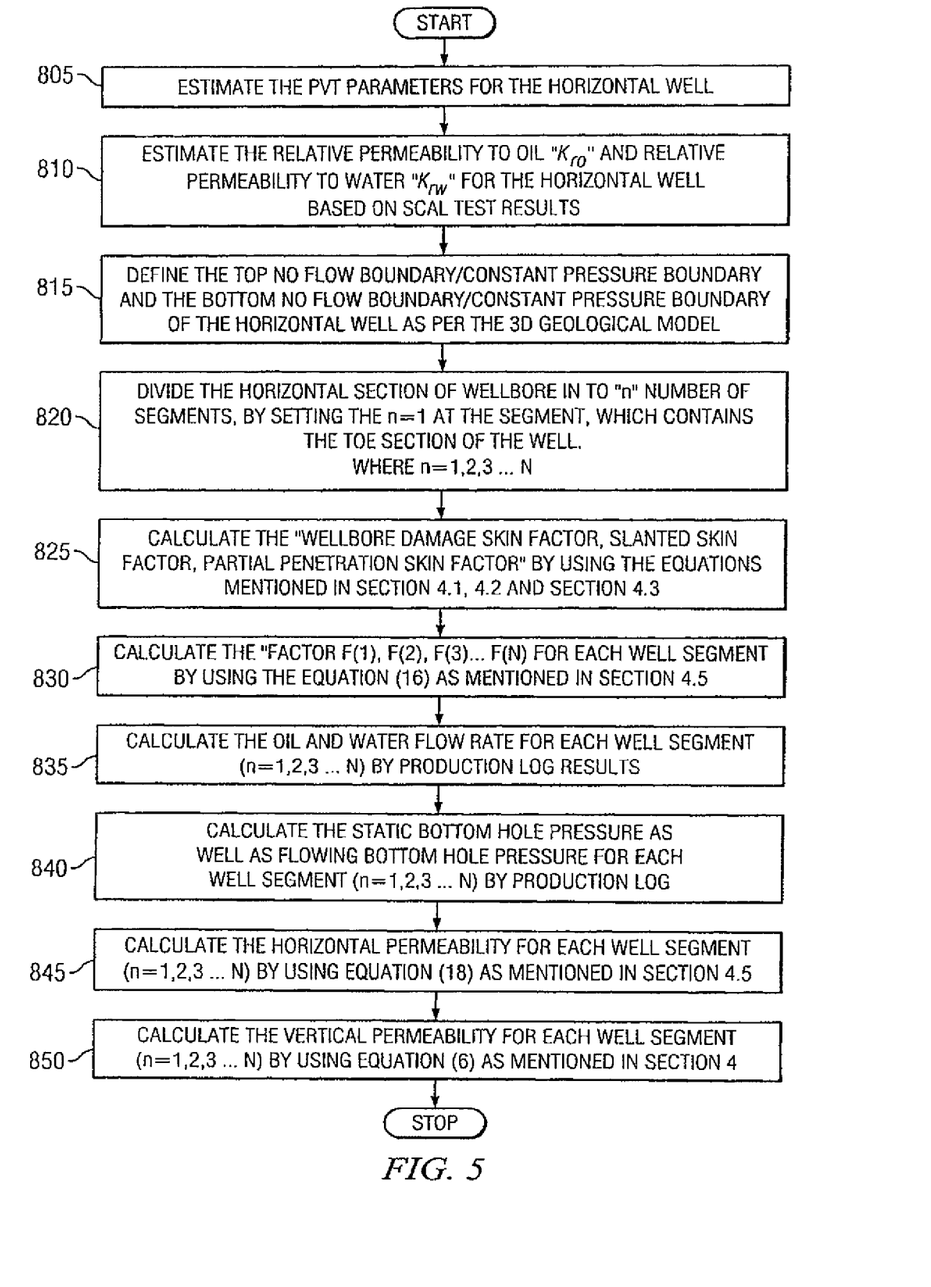
FIG. 5 illustrates a methodology for permeability calculation of a horizontal well using production logs, in accordance with a particular embodiment of the present disclosure.

FIG. 5 illustrates a method for determining permeability of a wellbore, that may be used in conjunction with the teachings of the present disclosure. It should be appreciated by those of ordinary skill in the art that the method described in FIG. 5 includes many optional steps and specific equations that may not be necessary to accomplish the spirit of the methods disclosed herein. In general, the method described in FIG. 5 uses data from multiple sources including fluid sample analyses, core sample analyses, 3D geological models (e.g., seismic analysis), and/or "actual" data regarding the well obtained from, for example well production logging tools.

The method of FIG. 5 begins at step 805 where fluid properties regarding the horizontal well are estimated. Such estimates are typically based upon fluid samples that are collected at or near the site of the horizontal well, and analyzed and/or calculated in a laboratory. Fluid properties that may be used in conjunction with the method described in FIG. 5 include pressure, volume and temperature (PVT parameters) of collected fluids.

At step 810, the relative permeability to oil and the relative permeability to water are estimated for the horizontal well. These estimates are typically based upon an analysis of core samples taken at or near the horizontal well, for example special core analysis (SCAL).

Next, at step 815, the top no flow/constant pressure boundary and the bottom no flow/constant pressure boundary of the horizontal well are estimated. These estimates are typically based upon a 3D geological model (e.g., 3D seismic analysis) of an area that surrounds and/or includes the horizontal well.

In order to perform the calculations of the present disclosure, the horizontal well is divided into a plurality of well segments, at step 820. The size of the segments can vary greatly within the teachings of the present disclosure but will typically be within the range of several inches, to several feet, and are typically measured approximately horizontally. The number of segments desirable to obtain a relatively accurate calculation will vary depending upon the size of the horizontal well, and how widely the horizontal well varies with respect to its properties, over a horizontal distance.

Beginning at step 825, horizontal well trajectory, horizontal well geometrical data, and basic reservoir and well design specifications are used to determine additional information regarding the horizontal well. For example, at step 825 the wellbore damage skin factor, slanted skin factor and partial penetration skin factor are determined. The wellbore damage skin factor, slanted skin factor and partial penetration skin factor are quantities that a person of ordinary skill in the art will be able to calculate. Example formulas for calculating these quantities is provided in the present disclosure (see equations (7) through (10)).

At step 830, a multiplication factor is calculated for each of the plurality of well segments. An example equation that may be used to calculate the multiplication factor is disclosed in the present disclosure (see equation (16), above).

Next, at step 835, the oil flow rate and water flow rate for each of the plurality of well segments are determined using production log results (e.g., obtained from production logging tools). The production log results may also be used to calculate the static bottom hole pressure as well as flowing bottom hole pressure for each of the well segments, at step 840.

Finally, at step 845, the horizontal permeability for each well segment may be calculated according to aspects of the present disclosure. For example, the equation disclosed above (see equation (18)) may be used to perform these calculations. The horizontal permeability for each well segment may be helpful in determining additional information regarding dynamic reservoir characterization, the horizontal well and/or designing drilling and completion systems associated with the horizontal well and adjacent well reservoir parameters of oil and gas fields. The permeability calculated from this method can determine the influence of fractures, faults, and high flow conduits on the multi-phase flow inside the reservoir. In accordance with a particular embodiment of the present disclosure, the horizontal permeability may be used as a key factor in improved inflow control device design and other advanced well completion design.

At step 850, the vertical permeability for each of the plurality of well segments may be optionally determined if desired. A sample equation that may be used to calculate the vertical permeability is disclosed above (see equation 6, above).

Absolute and Effective Permeability:

Embodiments of the present disclosure may also be used to evaluate the effective permeability profile or absolute permeability profile across the entire horizontal section of horizontal wellbore for oil, water and gas phase, based on the water saturation profiles predicted from sigma logs combined with production log data as well as water, oil and gas flow rate profiles estimated from production logs. "Absolute permeability" is also known in the art as "intrinsic permeability," which is a measure of the ability to transmit or conduct fluids through a rock, conducted when a single fluid, or phase, is present in the rock. "Effective permeability," on the other hand, is the ability to preferentially conduct or transmit a particular fluid when other fluids are present in the rock. The relative saturations of the fluids as well as the nature of the rock (or reservoir) have an impact upon the effective permeability.

The relationships between the effective and absolute permeability are given in the following equations from (19) to (21) for oil, gas, and water, respectively.

$$k_o = k_h k_{ro} \quad (19)$$

$$k_g = k_h k_{rg} \quad (20)$$

$$k_r = k_h k_{rw} \quad (21)$$

Where $k_o$, $k_g$, $k_w$, are absolute permeabilities for oil, gas, and water, respectively; and $k_{ro}$, $k_{rg}$, $k_{rw}$ are relative (effective) permeabilities for oil, gas, and water, respectively. As discussed above, the effective horizontal permeability for each segment of horizontal wellbore is calculated by using equation (18) above, and thereby the absolute permeability of oil, water and gas phase can be calculated by using equations (19) through (21), respectively.

Many of the calculations, estimations and determinations referred to above include some level of uncertainty, as with any estimation. The degree of uncertainty can vary widely and depends upon the accuracy of the data collected, the number of samples, the sophistication of measuring equipment, among many other factors. Such uncertainty regarding many of the input variables results in an effect on permeability calculations for the teachings of the present disclosure due in part, to some of the rational explained below. In the calculation of permeability, several simplifying assumptions are made, but the resulting errors are generally second order in nature and do not have a particularly significant effect on the results.

The potential uncertainties in the variables which can affect the permeability calculations include the following:

Fluid Properties—

The product of μo and Bo and μw and Bw changes little over the typical range of pressures and usually is known to within 3%-5% accuracy. Its effect on calculated permeability is relatively insignificant. However, in order to reduce the potential errors, the fluid property values may be used at the shut-in bottom hole pressure recorded from the production logs.

Pressures—

An error in drawdown will typically cause a proportional error in calculated permeability. In many cases, it is possible to assess stabilized drawdown within 5%-10% uncertainty. A potential source of inaccuracy in this technique is the lack of measurement stability. Normally, assessing the layer pressure by use of the SIP (Shut-In-Pressure) technique is possible to within approximately 2% of the true value. The stabilization time required for the flowing tests may sometimes be an issue. The well may be opened to flow with production logging tools above all perforations that then monitor rates and pressures for stability with a real-time, log-log, pressure-derivative graph before commencing flowing tests. When analyzing historical data for which this procedure was not done, pressure stability may be assessed by comparing pass-to-pass, pressure repeatability.

Drainage Radius, effective drainage width (w) and Wellbore Radius—

A 20% difference in either radius typically makes approximately a 0.5% to 1% difference in calculated permeability.

Flow Rate—

When possible, an attempt is made to flow the well through a test separator during a production logging tool test, but this is not always possible because of operational constraints. The production logging tool tests that are conducted with stable flow measured with accurate surface meters typically will approximately match the surface rates with a difference of less than 10%. This again has a relatively negligible effect on the calculated permeability.

Skin Factor—

The skin factor calculated from the methodology described above typically provides relatively accurate values of skins, in the case of horizontal wells. However, the other skin factors due to various completion types should be considered and estimated and added to these skin values in order to determine more accurate permeability values.

Furthermore, in order to determine the skin factors, the fluid production profiles and flowing bottom hole profiles can be generated by conducting the production logging at multiple chokes and at various flow rates. The skin values for each well segment can be calculated based on the pressure transient analysis (PTA analysis) methods for multiple flow rate tests.

Figure 6:
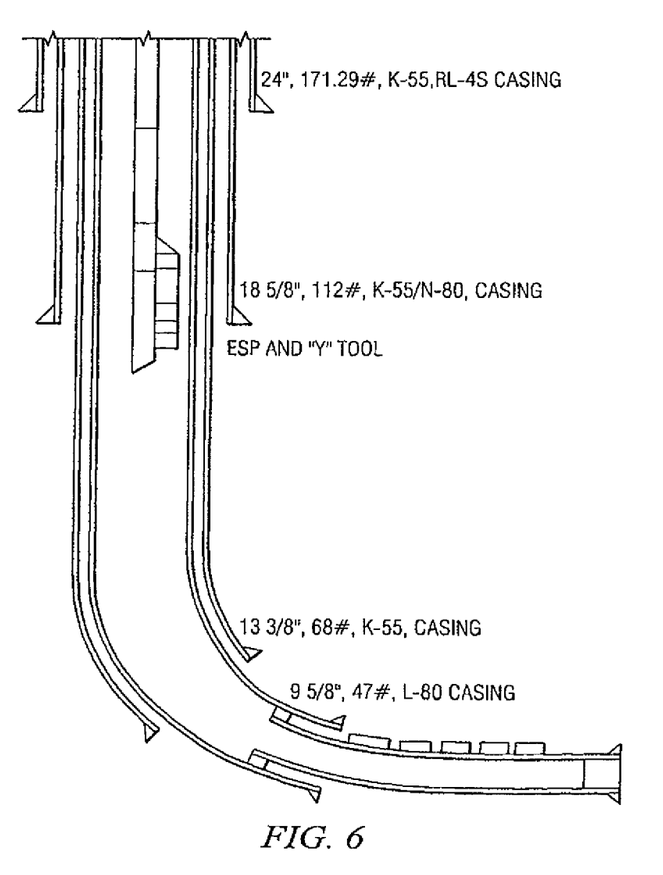
FIG. 6 illustrates an alternative embodiment horizontal well, in accordance with a particular embodiment of the present disclosure.

Many of the measurement, techniques, equations and calculations discussed herein were applied in field conditions to determine the permeability for a horizontal well (hereinafter, "Well A"). The well schematic for Well A is illustrated in FIG. 6.

Figure 7:
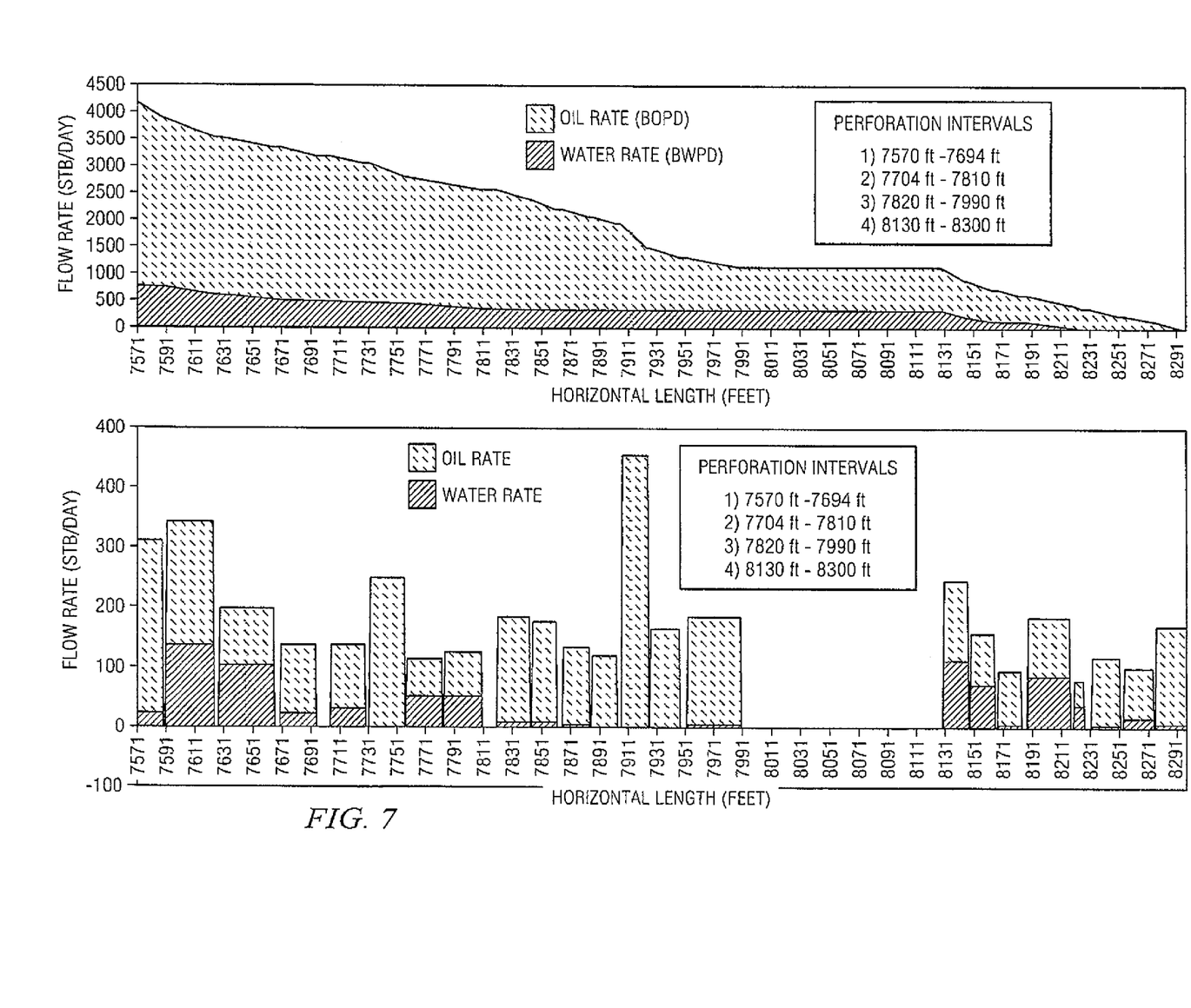
FIG. 7 illustrates a snapshot of a production log associated with the alternative embodiment horizontal well in accordance with a particular embodiment of the present disclosure.

The production log on this well was conducted at the total rate of about 5000 stock tank barrels/Day (STB/Day). A snapshot of the production log is depicted in FIG. 7. The oil and water production rates are marked on the production log of FIG. 7.

With regard to "Well A," the following describes some of the major steps carried out for permeability calculations.

1. The wellbore was divided into 728 segments with segment lengths of approximately 1 foot each.
2. The oil and water rate were estimated from the production log for each well segment.
3. The reservoir was determined to have a planar OWC @5860 ft TVDSS, which was assumed as the constant pressure boundary.
4. The impermeable layer (e.g., shale barrier) at the top of reservoir was assumed as the no flow boundary.
5. Based on the special core test analysis data, the oil and water relative permeability curves were generated for "Well A".
6. The permeability at each well segment was calculated based on the methods outlined above and detailed in the flow chart presented in FIG. 5.

Figure 8:
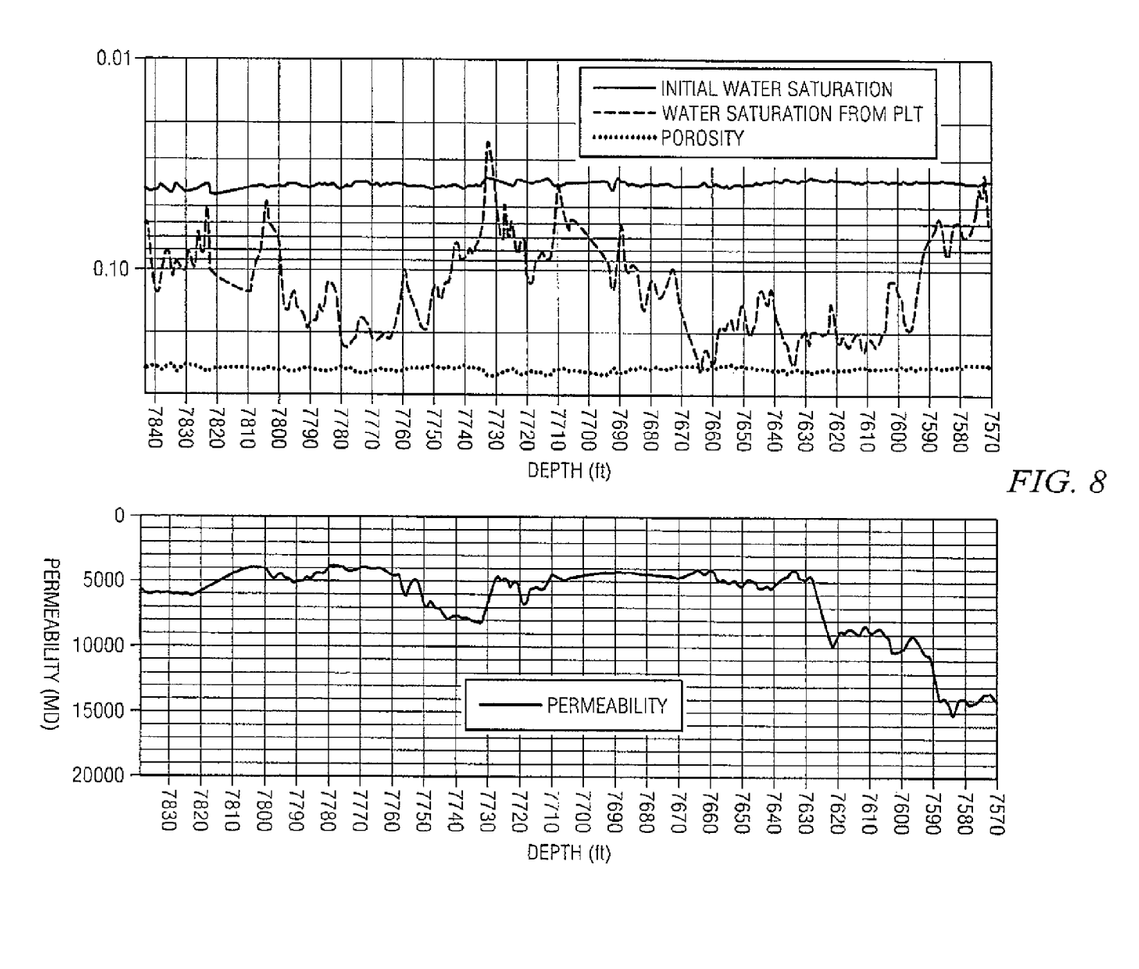
FIG. 8 illustrates a graph including formation permeability of the alternative embodiment horizontal well from a production log, in accordance with a particular embodiment of the present disclosure.

FIG. 8 illustrates a sample of results obtained in accordance with a particular embodiment of the present disclosure. The first track of the left hand side represents the initial water saturation, the second track of the left hand side represents the water saturation when the PLT was carried out, and the third track in the left hand side represents the porosity. The first track in the right hand of the plot represents the calculated permeability based on the methods outlined in the present disclosure.

Figure 9:
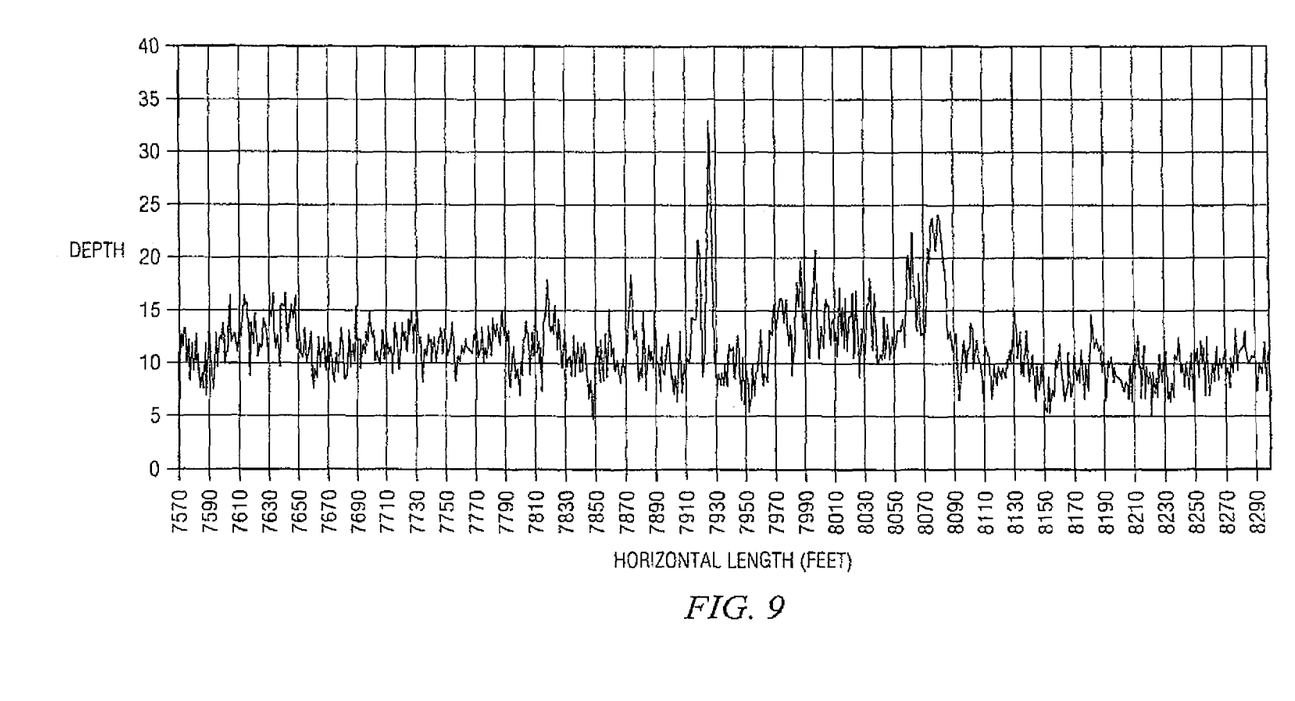
FIG. 9 illustrates a gamma ray plot of the alternative embodiment horizontal well, in accordance with a particular embodiment of the present disclosure.

It can be observed from FIG. 8 that the variation in the porosity as well as the initial water saturation for the horizontal section of "Well A" is very small. However, the permeability calculated from the methods outlined in this disclosure shows significant variation in the permeability values. Further, the water saturation values obtained from the sigma log of PLT shows significant variation and follows the permeability patterns as shown in FIG. 8. Normally the permeability values derived from the log do not show a significant difference in permeability values with small variations in porosity. Also the Gamma Ray profile shown in FIG. 9 is more or less uniform, and shows the clean uniform sand.

Therefore, the large variations in the permeability across the horizontal section revealed that, there are some faults and fractures (i.e., high flow units exist in the reservoir across the horizontal wellbore section).

In order to study the better reservoir characteristics, the obtained permeability profiles as shown in FIG. 8 were plotted on the 3D high resolution seismic. The 3D high resolution Seismic cross-section of "Well A" is shown in FIG. 10.

Figure 10:
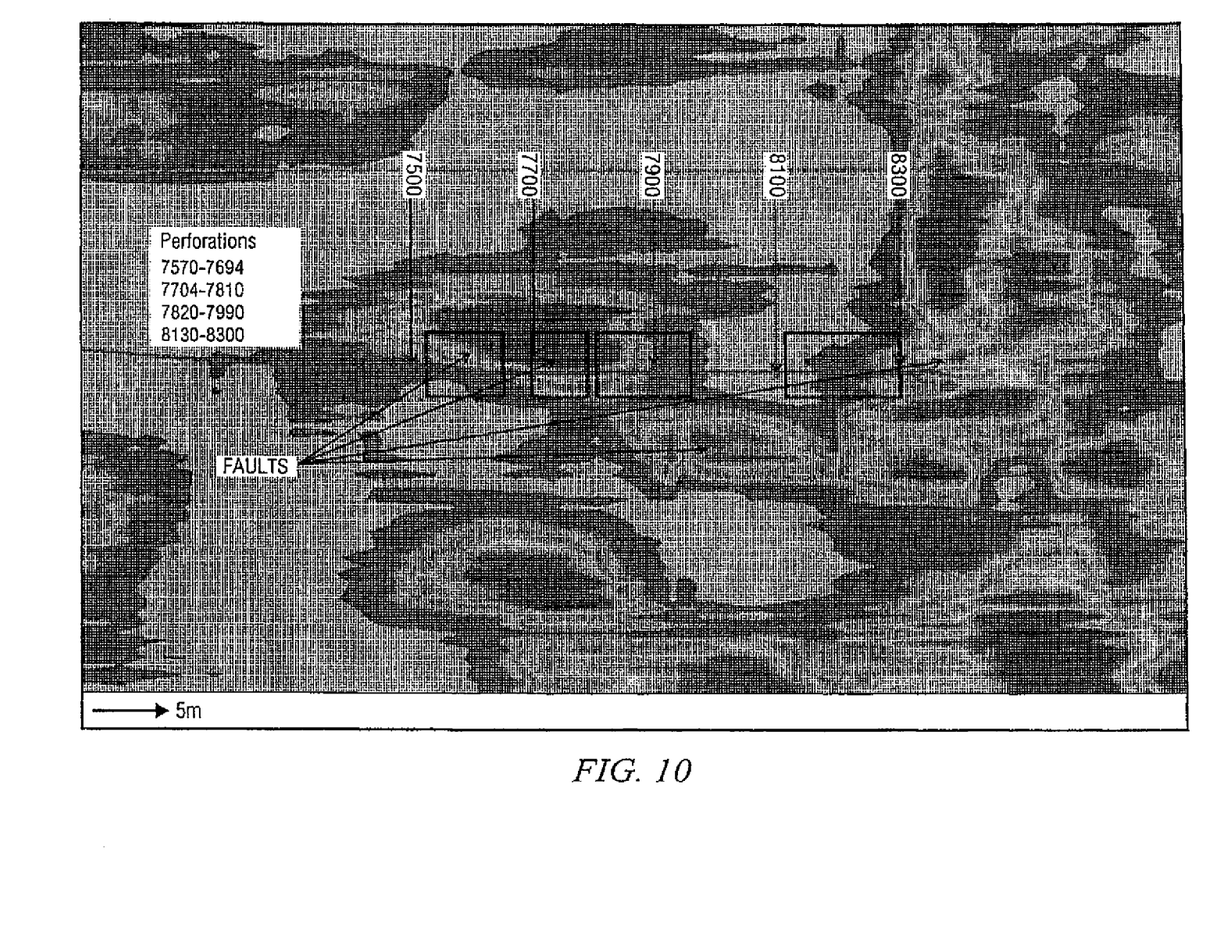
FIG. 10 illustrates a seismic cross section through the alternative embodiment horizontal well, in accordance with a particular embodiment of the present disclosure.

After comparison of FIG. 8 and FIG. 10, it can be concluded that the high permeability values correspond to faults and fractures associated with high flow units, which is the major conduit for premature water breakthrough in "Well A".

In view of the above it can be concluded that the, permeability values obtained from the method of this disclosure revealed the insights of the formation characteristics relatively well, which in turn describes the fluid movement and reservoir dynamics.

The permeability values obtained from the embodiment of the disclosure were utilized in the ICD (Inflow Control Device) well completion design by utilizing the Multi segment, Multiphase well models. The results are summarized below.

1. The nozzle size of each ICD module has been improved and customized for each segment across the entire horizontal wellbore in order to reduce premature water coning/water breakthrough.
2. The improved production rate with ICD completion has been established, which delayed the water breakthrough significantly.
3. The placement of swell packers in order to have an optimum number of wellbore compartments for ICD completions was determined.

4. The simulated wellbore pressure profiled was made uniform by using the optimum nozzle size and wellbore compartments.
5. The calculated permeability from the above mentioned techniques with the help of 3D high resolution seismic will be further utilized to improve the subsurface well locations of future wells as well as the improvement of well trajectory.
6. The future well trajectory of Intelligent Multilateral wells with ICD and ICV completions will be improved based on the above mentioned techniques.
7. The log derived permeability was calibrated based on the proper extrapolation techniques, in order to populate the permeability values in the 3D Geological Model and 3D High resolution Seismic models.

A good correlation generally exists between initial water saturation and permeability as explained by various investigators and as detailed in the following publication:

Carlos F., Haro, SPE, Occidental Oil & Gas, "The Perfect Permeability Transforms Using Logs & Cores" presented at the SPE annual Technical Conference and Exhibition, Houston, Tex., USA, September 2004.

Further the clay or shale effects and cementation may be important in permeability modeling. The permeability is affected by matrix cementation as well as the clay or shale percentage in the reservoir rocks. By considering all of these factors, a general correlation between permeability calculated from PLT, porosity, initial water saturation and clay or shale percentage (Vshale) may be developed and detailed as follows.

$$(\mathrm{Log}_{10}A)^a (\mathrm{Log}_{10}k)^b = f(\mathrm{Log}_{10}A) \quad (22)$$

Where, $$A = \frac{\phi^2 (1-s_{wi})(1-Vshale)^{Vshale/2}}{s_{wi}^2} \quad (23)$$

$$A = \frac{\phi^2 (1-s_{wi})(1-Vshale)^{Vshale/2}}{s_{wi}^2}$$

And, $f(\mathrm{Log}_{10} A)$ is the polynomial function of $[(\mathrm{Log})] 10 A$. Further the "a" and "b" are constants.

Figure 11:
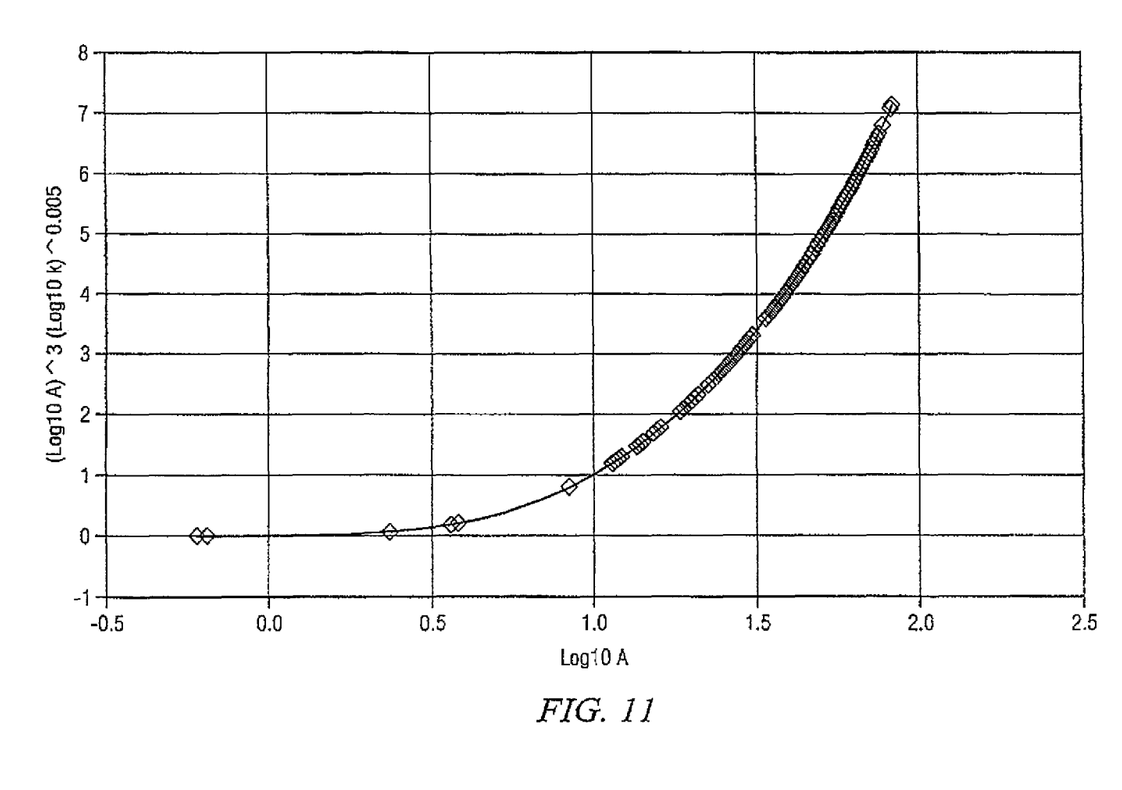
FIG. 11 illustrates a correlation among permeability, effective porosity, initial water saturation and clay percentage, associated with the alternative embodiment horizontal well, in accordance with a particular embodiment of the present disclosure.

In the case of Well A, the correlation between permeability calculated from PLT of Well A, effective porosity, initial water saturation and Vshale was obtained based on the above equations (22) and (23), and is detailed in following equation and presented in FIG. 11.

$$(\mathrm{Log}_{10}A)^3 (\mathrm{Log}_{10}k)^{0.005} = 1.00983(\mathrm{Log}_{10}A)^3 - 0.00768 (\mathrm{Log}_{10}A)^2 + 0.003350(\mathrm{Log}_{10}A) + 0.0007635 \quad (23)$$

FIG. 11 illustrates that a relatively good match was found between the calculated permeability of horizontal "Well A" and effective porosity, initial water saturation and clay percentage (Vshale).

The correlations detailed in equation (23) were used to calculate the permeability of new drilled horizontal wells based on the wire log data such as porosity, initial water saturation, etc.

Moreover, in accordance with the present disclosure, a relatively good match was found between core permeability and predicted permeability from the methods and systems disclosed herein. Further, the features like preferential flow units for water breakthrough, channels and faults were confirmed after plotting the real permeability data on the 3D high resolution seismic.

In summary, the methodology of permeability profile estimation for horizontal wells based on the methodology of this disclosure suggests/confirms the following:

The actual and relatively accurate permeability profile on a foot by foot basis for horizontal "Well A" was predicted based on the multiphase horizontal well production logging data.

The absolute permeability for oil phase, water phase and gas phase was predicted based on the calculated permeability profiles from production logging.

The potential flow units across the entire horizontal wellbore section were identified.

Faults, fractures and very high permeability sections along the horizontal wellbore were predicted and were in agreement with 3D high resolution Seismic.

The permeability values obtained from a particular embodiment of the present disclosure were utilized in the ICD (Inflow Control Device) well completion design by utilizing the multi segment, multiphase well models.

The calculated permeability from the techniques of the present disclosure along with the 3D high resolution seismic were utilized to improve the subsurface well locations of future wells.

The future well trajectory of Intelligent Multilateral wells with ICD and ICV completions may be improved/optimized based on the above mentioned techniques.

The log derived permeabilities were adjusted based on proper extrapolation techniques as detailed in particular embodiments of the present disclosure.

Numerous other changes, substitutions, variations, alterations and modifications may be ascertained by those skilled in the art and it is intended that the present disclosure encompass all such changes, substitutions, variations, alterations and modifications as falling within the spirit and scope of the appended claims.

Moreover, the present disclosure is not intended to be limited in any way by any statement in the specification that is not otherwise reflected in the claims. As an example, although the methods described below are described primarily with respect to horizontal wells, these methods are generally applicable to all types of formations and reservoirs.

NOMENCLATURE $a_{max}$=half length of the horizontal axes of damaged zone at the heel, ft
B=Formation Volume Factor, RB/STB
b=a variable to approximate cone shape equation
Ct=System Compressibility, (1/Psi)
ESP=electrical submersible pump
g=acceleration due to gravity, 32 ft/sec$^2$
h=true vertical length of well segment, ft
$h_1$=thickness from top of layer to top of well segment, ft
$h_m$=measured length of well segment, ft
$h_p$=length of production interval, ft
$I_{ani}$=permeability anisotropy, dimensionless
$J_s$=specific productivity index of an anisotropic media, STB/day/psi/ft
$J_s(i)$=specific productivity index in the middle of segment i, STB/day/psi/ft
k=effective permeability, md
$k_s$—effective permeability in damaged zone, md
$k_v$=vertical permeability, md
$k_h$=horizontal permeability, md
L=horizontal wellbore length, ft
M=Mobility ratio
n=number of segments
OWC=oil water contact $P_i$=reservoir pressure at oil water contact, psi
$P_r$=reservoir pressure at boundary, psi
$P_{wf}$=wellbore pressure at heel, psi
$P_w$=wellbore pressure, psi
$P_w(i)$=wellbore pressure at the boundary of segment i-1 and i, psi
q=flow rate, STB/day
q(i)=production rate from segment i, STB/day
$q_s$=production rate per unit length of the wellbore STB/day/ft
Q=total production rate, STB/day
$r_e$=drainage radius, ft
$r_w$=wellbore radius, ft
$r_{wD}$=dimensionless wellbore radius, ft
$S_r$=partial penetration skin factor
$S_\theta$=slant skin
S(i)=formation damage skin factor in the middle of segment i, STB/day
S=other skin factors
$S_{wi}$=irreducible water saturation, fraction
T=Time, hours
w=reservoir width, ft
x=distance in x direction, ft
x(i)=distance of middle of segment I from the toe, ft
Δx=well segment length, ft
y=distance in y direction, ft
z=distance in z direction, ft
μ=viscosity, cp
∅=porosity
$\lambda_o$=mobility of oil
$\lambda_w$=mobility of water
$\rho_o$=density of oil, pounds/ft³
$\rho_w$=density of water, pounds/ft³
Δρ=density difference between water and oil, pounds/ft³
Δγ=specific gravity difference between water and oil

What is claimed is:

1. A downhole measurement tool, comprising:
a downhole tool configured for insertion into and retraction from a horizontal well under downhole production logging conditions, said horizontal well being divided into plurality of well segments, wherein said downhole tool comprises:
   means for measuring fluid properties associated with the horizontal well, wherein the measured fluid properties associated with the horizontal well comprise estimated pressure, estimated temperature and estimated volume characteristics based upon fluid samples obtained from an area adjacent the horizontal well; and
   means for measuring actual production logging data associated with the horizontal well;
means for determining an approximate upper boundary and an approximate lower boundary of the horizontal well;
means for calculating relative permeability of oil and relative permeability of water for the horizontal well;
means for calculating a horizontal permeability for an i-th well segment as $$\frac{q_0(i)+q_w(i)}{\frac{k_{rO}}{\mu_0 B_0}+\frac{k_{rw}}{\mu_w B_w}},$$

where $q_0(i)$ is a measured oil production rate for the i-th well segment, $q_w(i)$ is a measured water production rate for the i-th well segment, $k_{rO}$ represents the measured relative permeability of oil, $k_{rw}$ represents the measured relative permeability of water, $\mu_0$ represents a measured oil viscosity, $\mu_w$ represents a measured water viscosity, $B_0$ represents a measured oil formation volume factor, and $B_w$ represents a measured water formation volume factor; and
means for displaying the calculated horizontal permeability for each said well segment.

2. The downhole measurement tool as recited in claim 1, further comprising a saturation log tool for measuring reservoir fluid saturations.

3. The downhole measurement tool as recited in claim 2, wherein the relative permeability of oil and the relative permeability of water are each calculated as estimates based upon the measured reservoir fluid saturations and core analysis performed upon core samples obtained from areas adjacent the horizontal well.

4. The downhole measurement tool as recited in claim 1, wherein the means for determining the approximate upper boundary and the approximate lower boundary of the horizontal well comprises means for determining boundaries based upon a scheme selected from the group consisting of: a three-dimensional geological model of an oil field area that includes the horizontal well, a seismic model of the oil field area that includes the horizontal well, and a well test interpretation of the oil field area that includes the horizontal well.

5. The downhole measurement tool as recited in claim 1, wherein the actual production logging data comprises an oil flow rate and a water flow rate for each said well segment.

6. The downhole measurement tool as recited in claim 1, further comprising means for calculating a static bottom hole pressure and a flowing bottom hole pressure from a production logging survey for each said well segment.

7. The downhole measurement tool as recited in claim 1, further comprising means for calculating a wellbore damage skin factor.

8. The downhole measurement tool as recited in claim 1, further comprising means for calculating a slanted skin factor.

9. The downhole measurement tool as recited in claim 1, further comprising means for calculating a partial penetration skin factor.

10. The downhole measurement tool as recited in claim 1, further comprising means for calculating an absolute permeability for oil, an absolute permeability of gas and an absolute permeability of water for each said well segment.

11. The downhole measurement tool as recited in claim 1, further comprising means for calculating vertical permeability for each said well segment.

\* \* \* \* \*